United States Patent
Ali et al.

(10) Patent No.: US 11,607,381 B2
(45) Date of Patent: Mar. 21, 2023

(54) REMINERALIZATION OF TEETH USING BRAZILIAN GREEN PROPOLIS

(71) Applicant: Imam Abdulrahman Bin Faisal University, Dammam (SA)

(72) Inventors: Saqib Ali, Dammam (SA); Imran Farooq, Dammam (SA); Amr Bugshan, Dammam (SA); Intisar Ahmad Siddiqui, Dammam (SA); Khalifa S. Al-Khalifa, Dammam (SA); Mohammed Taha Ali Al-Hariri, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 108 days.

(21) Appl. No.: 17/234,241

(22) Filed: Apr. 19, 2021

(65) Prior Publication Data

US 2022/0331233 A1    Oct. 20, 2022

(51) Int. Cl.
| | |
|---|---|
| *A61K 8/98* | (2006.01) |
| *A61K 8/14* | (2006.01) |
| *A61K 8/92* | (2006.01) |
| *A61Q 11/00* | (2006.01) |
| *A61K 8/21* | (2006.01) |
| *A61K 8/19* | (2006.01) |
| *A61K 8/24* | (2006.01) |

(52) U.S. Cl.
CPC .............. *A61K 8/988* (2013.01); *A61K 8/14* (2013.01); *A61K 8/19* (2013.01); *A61K 8/21* (2013.01); *A61K 8/24* (2013.01); *A61K 8/922* (2013.01); *A61Q 11/00* (2013.01)

(58) Field of Classification Search
CPC .......... A61Q 11/00; A61K 8/988; A61K 8/14; A61K 8/19; A61K 8/21; A61K 8/24; A61K 8/922
See application file for complete search history.

(56) References Cited

U.S. PATENT DOCUMENTS

2018/0177695 A1 * 6/2018 Miller ................. A61K 8/03

FOREIGN PATENT DOCUMENTS

| | | | |
|---|---|---|---|
| CA | 2 705 299 A1 | 8/2009 | |
| CN | 107412138 A * | 12/2017 | ............... A61K 8/24 |
| ID | 2018/S/01247 S | 12/2018 | |
| RU | 2 197 951 C1 | 2/2003 | |
| WO | WO 2013/091053 A1 | 6/2013 | |
| WO | WO-2013095366 A1 * | 6/2013 | ............... A61K 8/19 |
| WO | WO-2016007629 A2 * | 1/2016 | ............. A61C 19/06 |
| WO | WO 2017/072105 A1 | 5/2017 | |
| WO | WO-2017072104 A1 * | 5/2017 | ............... A61K 8/21 |
| WO | WO 2017/219339 A1 | 12/2017 | |

OTHER PUBLICATIONS

Liu, Machine translation of CN-107412138-A, 2017 (Year: 2017).*
Bencze, Machine translation of HU 194737 B, Process for Extracting All the Active Substances of Propolis and for Preparing Compositions Containing the Same (Year: 1988).*

(Continued)

*Primary Examiner* — Adam C Milligan
*Assistant Examiner* — Amanda Michelle Petritsch
(74) *Attorney, Agent, or Firm* — Oblon, McClelland, Maier & Neustadt, L.L.P.

(57) ABSTRACT

Method for remineralizing teeth or increasing hardness of tooth enamel by application of Brazilian green propolis oil or its components.

13 Claims, 4 Drawing Sheets

(56) References Cited

OTHER PUBLICATIONS

Risqa Rina Darwita, et al., "The Comparison Effect of CPP-ACP containing Propolis and CPP-ACP without Propolis on the Number of *Streptococcus mutans* in White-spot Enamel Surface", The 4th Biomedical Engineering's Recent Progress in Biomaterials, D Rugs Development, Health, and Medical Devices AIP Conference Proceedings, vol. 2193, 2019, pp. 030007-1-030007-5.
Muhamad Sahlan, et al., "Formulation of microemulsion propolis fluoride (PF) as varnish topical agent to stop activity of teeth caries", AIP Conference Proceedings, vol. 1817, Issue 1, 2017, 6 pages (Abstract only).
E. A. Ophori, et al., "Antimicrobial activity of propolis against *Streptococcus mutans*", African Journal of Biotechnology, vol. 9, No. 31, Aug. 2, 2010, pp. 4966-4969.
Simone Duarte, et al., "The influence of a novel propolis on mutans streptococci biofilms and caries development in rats", Archives of Oral Biology, vol. 51, 2006, pp. 15-22.
J.P. Chu, et al., "Effect of compounds of *Galla chinensis* on remineralisation of initial enamel carious lesions in vitro", Journal of Dentistry, vol. 35, Issue 5, May 2007, pp. 383-387 (Abstract only).
Adriana Andrade Carvalho, et al., "In vivo antitumoural activity and composition of an oil extract of Brazilian propolis", Food Chemistry, vol. 126, 2011, pp. 1239-1245.
Saqib Ali, et al., "Efficacy of propolis in remineralising artificially induced demineralization of human enamel—An in-vitro study", Journal of Taibah University Medical Sciences, vol. 16, No. 2, 2021, pp. 283-287.

\* cited by examiner

REMINERALIZATION OF TEETH USING BRAZILIAN GREEN PROPOLIS

STATEMENT REGARDING PRIOR DISCLOSURE BY AN INVENTOR OR A JOINT INVENTOR

Aspects of this technology are described by Ali, S., et al., *Efficacy of propolis in remineralising artificially induced demineralisation of human enamel—An in-vitro study* J. TAIBAH UNIVERSITY MEDICAL SCIENCES, 2020, hypertext transfer protocol secure://doi.org/10.1016/j.jtumed.2020.10.022, which is hereby incorporated by reference for all purposes.

BACKGROUND OF THE INVENTION

Field of the Invention

The invention pertains to the fields of apiculture and dentistry.

Description of Related Art

Dental enamel constitutes the outer protective coating of teeth. Odontoblasts (cells responsible for producing dentine) are available throughout the life of a person. However, the ultimate fate of ameloblasts (cells that synthesize enamel) is apoptosis and regression. Thus, enamel cannot be biologically repaired or replaced after its formation.

Human teeth are continuously subjected to dynamic cycles of demineralization and remineralization. A balance between these two coupled processes is crucial for maintaining the tooth structure. When this equilibrium shifts in favor of demineralization, the risk of tooth surface loss is increased.

Interaction among multiple factors such as cumulative salivary flow, dietary habits of a person, and the oral microflora can significantly shift the balance towards demineralization. Moreover, constant consumption of acidic foods or drinks and low salivary flow rate over time generate an acidic environment with low pH, resulting in demineralization that can eventually lead to dental caries or erosion.

Certain systemic diseases such as gastro-esophageal reflux disease are also associated with demineralization of teeth, ultimately resulting in dental erosion. Interestingly, demineralization can be reserved in its early stages if the intensity and the frequency of acidic attack are reduced together with the creation of an oral environment that favors remineralization.

The potential of tooth surface remineralization could be increased naturally through salivary ions or it could be induced by therapeutic materials. Currently available remineralization therapies act either by increasing the minerals around the demineralized lesions or by affecting the volume and the composition of the dental biofilm around the lesions.

Among the currently available therapies, fluoride application is the standard management for remineralization of demineralized lesions, as it has the ability to replace hydroxyl ions in the apatite structure, changing it from hydroxyapatite (HAP) to fluorapatite (FAP). Chemically, FAP is more stable and resistant to acidic exposures.

Recently, products have been developed to enhance the remineralization ability by utilizing potential elements for remineralization such as calcium, phosphate, sodium trimetaphosphate, triclosan, and xylitol.

Propolis is an important natural product that has already shown its efficacy as an anti-inflammatory agent, anti-infective agent, and antioxidant. However, its capacity to induce remineralization of tooth enamel has not been explored and there is a scarcity of studies in the available literature regarding its potential as a remineralizing agent for tooth enamel.

As disclosed below, one objective of the inventors is to describe a method that hardens propolis oil and induces remineralization of tooth enamel.

The foregoing paragraphs have been provided by way of general introduction, and are not intended to limit the scope of the following claims. The described embodiments, together with further advantages, will be best understood by reference to the following detailed description taken in conjunction with the accompanying drawing.

BRIEF SUMMARY OF THE INVENTION

Aspects of the invention include but are not limited to the following.

A method for remineralizing teeth or for protecting or hardening tooth enamel comprising contacting a tooth of a subject with Brazilian green propolis oil. This method may be applied to remineralize a portion or particular surface of a tooth, such as the enamel, dentine, or cementum.

In many cases the subject to be treated has a carie or cavity, or an exposed tooth root due to recession of the gums, or other damaged, demineralized portion of a tooth, such as a fractured, eroded, or otherwise damaged tooth. Some subjects will have conditions that facilitate demineralization of teeth, such as reduced saliva flow or quantity or below normal (based on healthy subjects) pH, such as a pH below 7, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1 or 5.0. Saliva pH is preferably measured at least 1, 2, 3 or 4 hours after consumption of foods or beverages. The pH level where enamel and dentin can begin to erode is referred to as critical pH. Enamel can begin to erode at a pH ranging from 5.5-5.7, while dentin's critical pH is much higher at 6.0-6.9.

Some patients have diets which frequently expose them to acidic foods and beverages in amounts that demineralize teeth. In some cases, a subject will have periodontal disease, gum recession, inflammation of the teeth or gums, or abnormal oral microbial flora.

In some embodiments Brazilian green propolis oil or a composition containing it is contacted with teeth for at least 1, 2, 5, 10, 15, or 30, minutes or for 1, 2, 4, 6, 12, 18, 24 or more hours. For example, a shorter exposure may result from application of a paste or ointment to the teeth, while a longer exposure may be obtained by application of a film, varnish or paint. Trays that fit around the teeth may also be used to expose teeth to compositions containing Brazilian green propolis oil.

The Brazilian green propolis oil as used herein typically comprises a vegetable oil extract of Brazilian green propolis. However, in some embodiments mineral oils or other hydrophobic or non-ionic solvents may used. In a preferred embodiment, the Brazilian green propolis extract comprises canola oil.

The components of Brazilian green propolis that are extracted into the oil may be further isolated, for example, by chromatography or phase-partitioning. One example is partitioning of Brazilian green propolis oil in an alcohol or aqueous mixture of an alcohol, such as methanol or ethanol, substantially immiscible with the oil, and recovery of the fraction of propolis compounds partitioning into the aqueous alcohol. The isolated fraction of Brazilian green propolis may be used by itself, resuspended in oil, or admixed with other carriers or excipients.

In some embodiments, the Brazilian green propolis oil comprises 0.01, 0.02, 0.05, 0.1, 0.2, 0.5, 1.0, 2.0 to 5 wt % of phenolic acids or other phenolic compounds. This range, and other ranges disclosed herein, include all intermediate and terminal values as well as subranges.

In other embodiment the Brazilian green propolis oil comprises 0.01, 0.02, 0.05, 0.1, 0.2, 0.5, 1.0, 2.0 to 5 wt % of flavonoids.

In one embodiment, the Braziliang propolis oil comprises 0.01, 0.02, 0.05, 0.1, 0.2, 0.5, 1.0, 2.0 to 5 wt % of Artepillin C.

In some embodiments, other extracts of BGP may be used, for example, those extracted in hydroxy-3-prenylcinnamic acid, 3,4-dihydroxy-5-prenylcinnamic acid, isosakuranetin, kaempferide, dihydrokaempferide, and (E)-3-{-4-hydroxy-3-[(E)-4-(2,3-dihydrocinnamoyloxy)-3-methyl-2-butenyl]-5-prenylphenyl}-2-propenoic acid or those described by and incorporated by reference to Carvalho, et al., FOOD CHEMISTRY, 2011, 126(3), 1239-1245.

Propolis is formed by a complex set of components collected by *Apis mellifera* from different parts of plant resins (twigs, flowers, pollen, buttons, and exudates of trees) which are deposited in the hive with saliva and enzymes of the insect to seal the cracks and maintain the temperature. Standardized Brazilian green propolis products are commercially available, such as those sold by Apis Flora Company (hypertext protocol secure://www.apisflora.com.br/catalog last accessed Apr. 14, 2021).

Propolis comprises resins with about 40-60 wt % of the mixture being composed of flavonoids and phenolic acids usually about 50 wt %; about 25-35 wt % waxes, usually about 30 wt %; about 5-15 wt % essential oils usually about 10 wt %; and about 1-10 wt % pollen, usually about 5 wt %. Among the present compounds, it can be composed of hydrocarbons, alcohols, aliphatic and aromatic acids, esters and its derivatives, aldehydes, ketones, flavonoids, fatty acids, terpenoids, amino acids, sugars, lignans, vitamins, minerals, and other components.

The chemical composition of propolis differs significantly according to the geographic region where resins were collected due to the flora of each region, allowing the selection of different plants as source of resin. When this product is derived from Europe or China, for example, the main plant metabolites found are flavonoids and phenolic acids, unlike the stemmed ones from southeastern Brazil, which, besides phenolic compounds, contain high amounts of terpenoids and prenylated derivatives of p-coumaric acid. These differences in composition reveal the collection of resinous material in temperate zones from poplar, especially species of *Populus*; and in southeastern Brazil from *Baccharis dracunculifolia* DC (Compositae),

*Baccharis dracunculifolia* DC (Asteraceae) is the main botanical source used by honeybees to produce Brazilian green propolis.

Figure 2A:
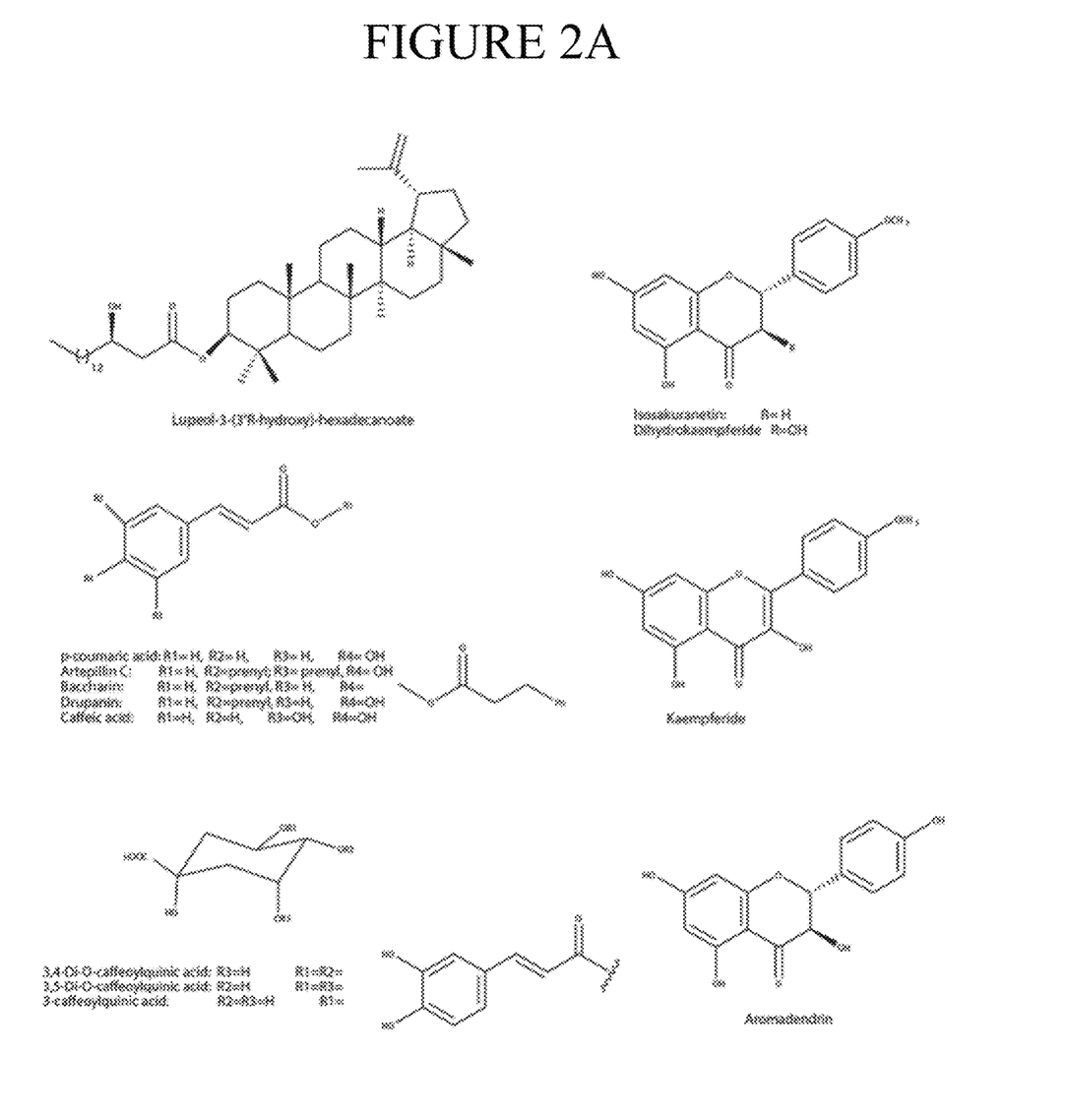
FIG. 2A describes the chemical structures of components of Brazilian green propolis.
Figure 2B:
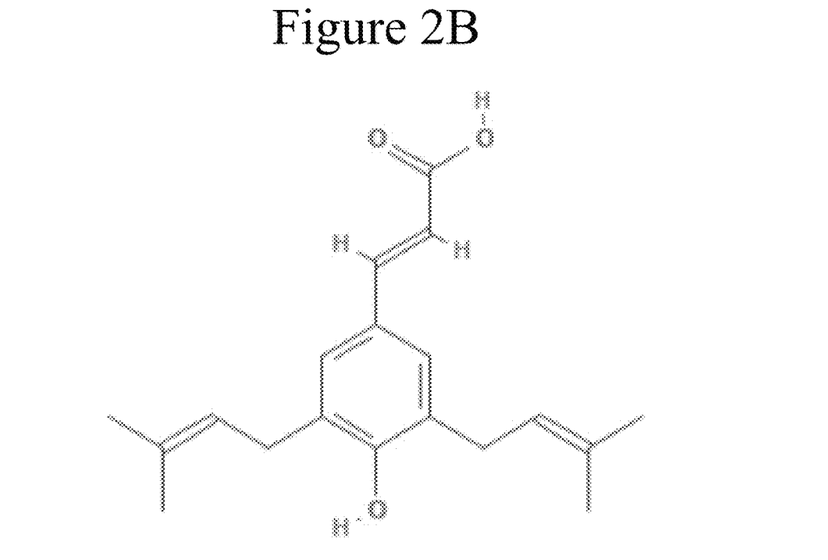
FIG. 2B describes the chemical structure of Artepillin C.
Figure 3:
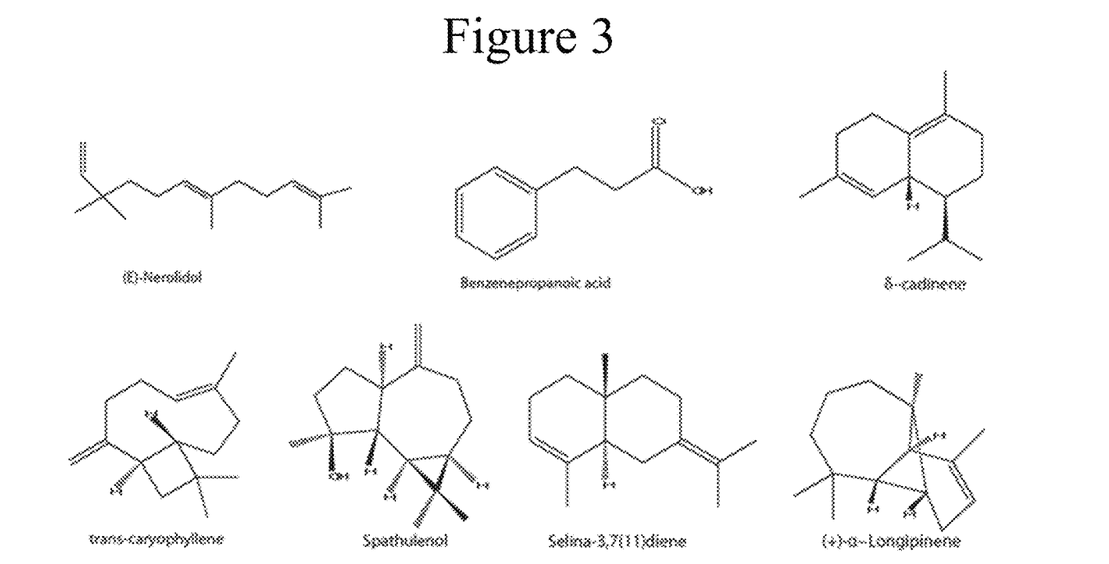
FIG. 3 describes the chemical structures of volatile components of Brazilian green propolis.

Brazilian green propolis is composed of large amounts of phenolic compounds such as artepillin C, baccharin, kaempferide, isosakuranetin, dihydrokaempferide, drupanin, p-couma ric acid, caffeic acid, aromadendrin, caffeoylquinic acid derivatives, and other compounds, such as the triterpene lupeol-3-(3'R-hydroxy)-hexadecanoate. The key source of these compounds is *B. dracunculifolia*. FIG. 2A describes the chemical structures of compounds found in Brazilian green propolis and FIG. 2B describes the chemical structure of Artepillin C a component of Brazilian green propolis.

The major volatile components of Brazilian green propolis are sesquiterpenes, such as (E)-nerolidol, β-caryophyllene, spathulenol, and δ-cadinene. Furthermore, other compounds such as selina-3,7(11)diene, benzenepropanoic acid and longipinene were also identified.

According to Fernandes-Silva, C. C., et al., J. Sci. Food Agric, 2015, 95, 309105, the main constituents of its volatile fraction are the phenylpropanoid 3-prenylcinnamic acid allyl ester (26.3%) and the sesquiterpene spathulenol (23.4%). It also contains several other sesquiterpenes and phenylpropanoids, in addition to linalool and α-terpineol (monoterpenes). Brazilian green propolis, its oil extract or oil extract fractions, in some embodiments may be characterized or standardized based on a the phenylpropanoid 3-prenylcinnamic acid allyl ester ranging from about 23-29 wt %, preferably about 26.3%, and 20 to 20 wt % sesquiterpene spathulenol preferably about 23.4 wt %. Standardization may be based on the content of these or other compounds such as Drupanin, Artepelin C and Bacharin as they appear in raw propolis, its volatile components, or its fractions, such as its oil fraction, ethanol fractions or aqueous fractions.

Figure 4:
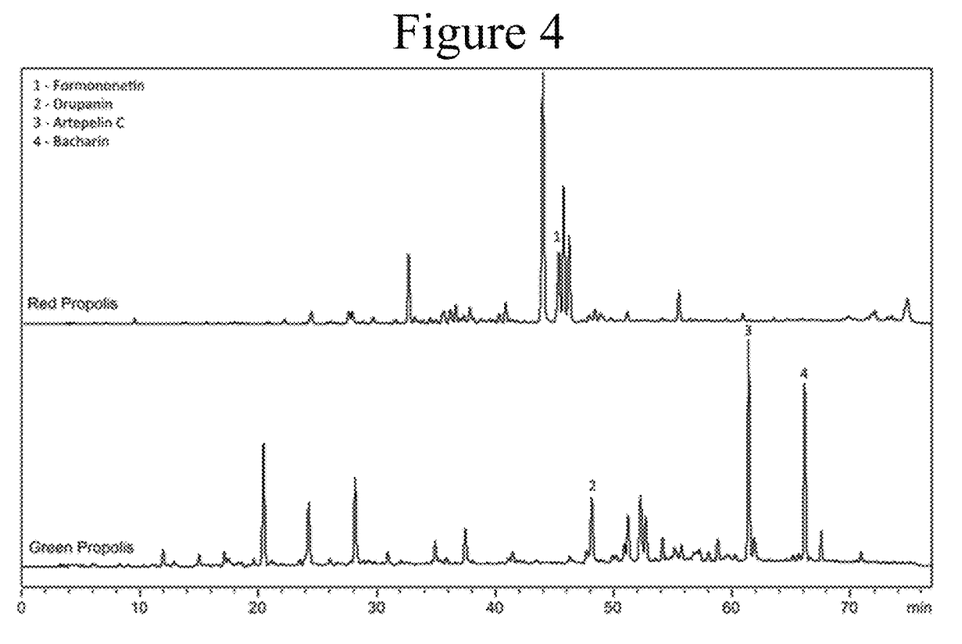
FIG. 4 describes the chemical fingerprints of red and green propolis.

As shown by FIG. 4, Brazilian green propolis contains little or no Formononetin but contains significant amounts of Drupanin, Artepelin C and Bacharin compared to red propolis. See Berretta, A. A., et al., *Functional Properties of Brazilian Propolis: From Chemical Composition Until the Market,* 2017, DOI: 10.5772/65932. Available from: hypertext transfer protocol secure://www.intechopen.com/books/superfood-and-functional-food-an-overview-of-their-processing-and-utilization/functional-properties-of-brazilian-propolis-from-chemical-composition-until-the-market (last accessed Apr. 2, 2021, incorporated by reference) for its description of the chemical composition of, functional properties of, distinguishing features of green propolis compared to other types of propolis, such as red or brown propolis, sources of, production of, and other description of Brazilian propolis. Those skilled in the art can determine the content ranges of these and other components of BGP in commercially available BGP, such as those available from the Apis Flora Co.

Another aspect of the invention is directed to a composition comprising Brazilian green propolis oil that optionally comprises one or more additional active agents, carriers, or excipients. The composition may be substantially hydrophobic, a mixture of hydrophobic and aqueous or polar components, or substantially aqueous or polar. Compositions include mixtures of oils, W/O or O/W emulsions, ointments or salves, pastes, liposomes, gels, foams, films, or varnishes. Brazilian green propolis oil compositions may contain other active ingredients, such as fluorides, calcium or phosphorous compounds, or inactive ingredients or excipients such as buffers, emulsifiers, or film-forming resins.

In some embodiments, the Brazilian green propolis oil is incorporated into artificial saliva.

In other embodiments the Brazilian green propolis oil or a composition containing it further comprises a calcium salt, a phosphorous salt, and/or a fluoride.

In some embodiments the Brazilian green propolis oil further comprises an amino acid, including but not limited to arginine and lysine, and/or a bioactive peptide.

The Brazilian green propolis oil is preferably incorporated into a microparticle or nanoparticle; a gel, foam, or spray; an emulsion, liposome, ointment, paste (e.g., toothpaste), salve; or a film, varnish, or paint that can be applied to the teeth.

DETAILED DESCRIPTION OF THE INVENTION

Propolis or bee glue is a resinous mixture that honey bees or *Apis mellifera* produce by mixing saliva and beeswax with exudate gathered from tree buds, sap flows, or other botanical sources. It is used as a sealant for unwanted open spaces in the hive and is used to fill small gaps of approximately 6 millimeters or less, while larger spaces are usually filled with beeswax. Propolis color varies depending on its botanical source, with dark brown as the most common. Propolis is sticky at and above 20° C., while at lower temperatures it becomes hard and brittle.

Brazilian green propolis—Brazilian green propolis is a specific type of propolis, which contains *Baccharis dracunculifolia* resin, as a main source. The typical compounds of Brazilian green propolis are prenylated derivatives of p-coumaric acid and of acetophenone, as well as diterpenes and lignans. These flavonoids differ from those in other kinds of propolis, such as poplar-type propolis. Brazilian green propolis also compositionally differs from red or brown propolis. The constituents of Brazilian green propolis have been distinguished from other types of propolis The typical components of poplar propolis are the phenolics: flavonoid aglycones, (flavones and flavanones), phenolic acids and their esters. The typical compounds of Brazilian propolis are prenylated derivatives of p-coumaric acid and of acetophenone, as well as diterpenes and lignans. Brazilian green propolis. As shown in FIG. 4, the chemical fingerprint of Brazilian green propolis differs from that of red propolis and contains components such as Drupanin, Artepelin C and Bacharin substantially absent from red propolis.

Propolis oil describes a propolis extract produced by dissolving propolis components into an oil, such as edible vegetable oil. Methods for obtaining propolis oil are described by B. Tosi, et al., *Antimicrobial activity of some commercial extracts of propolis prepared with different solvents*, Phytotherapy Res., 1996, 10, 335-336 or A. A. Carvalho, et al., *In vivo antitumoural activity and composition of an oil extract of Brazilian propolis*, FOOD CHEMISTRY, 2011, 126(3), 1239-1245 (both incorporated by reference). Brazilian green propolis oil is obtained by extraction of Brazilian green propolis. For example, propolis oil may be obtained by extraction of propolis in canola, peanut, soybean, or other vegetable oil, followed by filtration to remove solids.

Propolis may be suspended in oil, for example, by mechanical homogenization, by shaking or vortexing, or by sonication. Extraction may be continued for <1, 1, 2, 5, 10, 20, 24 or >24 hours at a temperature ranging from 0° C. to 100° C., preferably at room temperature 25° C. or less and at a temperature at which the extracting oil remains liquid.

Preferably, the suspension of oil and propolis is filtered, centrifuged or sedimented after extraction to remove solids to produce the propolis oil.

The oil extract may be further partitioned, for example in a mixture of an alcohol, like methanol or ethanol, and water followed by recovery and drying of the alcohol-water fraction. An extraction temperature may range from 0, 10, 20, 30, 40, 50, 60, 70, 80, 90, 100, to >100° C., preferably, at about 20, 25, to 30° C. The partitioning mixture of aqueous alcohol may contain <5, 10, 20, 30, 40, 50, 60, 70, 80, 90, 95 or >95% alcohol. For example, propolis oil may be extracted by phase-separation in 80% v/v methanol/water, followed by removal of the methanolic phase by drying to produced ODEP as described below.

The composition of ODEP (obtained with edible vegetable oil) or similar fractions may be further characterized by chromatographic separation and thin layer chromatography; see Carvalho, et al., Food Chem., 2011, 126 (3), 1239-1245 (incorporated by reference). Propolis oil may be standardized based on content of at least one component of propolis or propolis oil, including, but not limited to polyphenols, flavonoid aglycones, phenolic acid and their esters, caffeic acid and their esters and phenolic aldehydes and ketones.

Components isolated from propolis oil, such as those removed by phase partitioning into aqueous alcohol, may be reconstituted into the same or different oil as the parental propolis oil or admixed with other active ingredients, carriers or excipients.

Standardization of propolis oil. A standardized propolis oil extract may be obtained by extracting 50 grams of propolis in 500 ml of canola oil for 24 hours at 25° C. and removing solids. Raw propolis may be obtained from the same hive or hives or from hives in the same geographical area, such as hives within a 1, 5 or 10 kilometer radius. Raw propolis may be harvested during the same month or season. Propolis may be classified by type of bee, location of harvest, date of harvest, color, wax content, or content of other components.

The content of phenolic acids, phenolic compounds, flavonoids, or other components of Brazilian green propolis, such as Drupanin, Artepelin C and Bacharin in propolis oil, its fractions, or the propolis used to make it, may be used to standardize the compositions or functional properties of Brazilian green propolis oils or other extracts. Alternatively, Brazilian green propolis may be characterized by the geographical location of its sources and the time of year it was collected. Standardized BGP products are also commercially available, such as those from Apis Flora Co.

Different preparations of Brazilian green propolis oil or its fractions such as ODEP, may be standardized as described by Syukri, Y., et al., *Standardization of Specific and Non-Specific Parameters of Propolis Extract as Raw Material for Herbal Product*, EKSAKTA J. OF SCIENCES AND DATA ANALYSIS, 2020, 1(1), 36-43 (incorporated by reference).

In one embodiment, the content of the phenolic compound Artepillin C is used to standardize a propolis oil extract or derivative thereof such as ODEP; see Beserra, F. P., et al., *Artepillin C as an outstanding phenolic compound of Brazilian green propolis for disease treatment: A review on pharmacological aspects*, 2020, hypertext transfer protocol secure://doi.org/10.1002/ptr.6875 (incorporated by reference) or Serafini, et al., U.S. Pat. No. 10,888,590 (incorporated by reference).

Compositions. As referenced herein, an "oral care composition" is any composition that is suitable for administration or application to the oral cavity of a human or animal subject for enhancing health, hygiene or appearance of the subject, preferably providing such benefits as the prevention or treatment of a physiologic condition or disorder such as erosion or demineralization of teeth, the provision of sensory, decorative or cosmetic benefits, and combinations thereof. In various embodiments, an oral care composition is not intentionally swallowed, but is rather retained in the oral cavity for a time sufficient to affect remineralization or to otherwise protect enamel. Preferably, specific materials and compositions to be used as disclosed herein are, pharmaceutically- or cosmetically-acceptable. As used herein, such a "pharmaceutically acceptable" or "cosmetically acceptable" component, or a component used in a "safe and effective amount", is one that is suitable for use with humans and/or animals to provide the desired therapeutic, prophylactic, sensory, decorative, or cosmetic benefit without undue adverse effects (such as toxicity, irritation, and allergic response) commensurate with a reasonable benefit/risk ratio.

Propolis oil compositions. Propolis oil may be prepared in a variety of compositional forms. Preferably, propolis oil is produced by extraction or suspension of propolis, such as Brazilian green propolis, in a non-ionic solvent, such as vegetable oil; e.g., canola oil, corn oil, sunflower oil, safflower oil, peanut oil, olive oil, soybean oil, nut oils, cottonseed oil, sesame oil, palm oil, coconut oil, or cocoa oil. Other oils may be used including those described by hypertext transfer protocol//en.wikipedia.org/wiki/Vegetable oil (last accessed Mar. 29, 2021, incorporated by reference). In some embodiments, a mineral oil, animal fats and oils, or processed oils such as hydrogenated oils, may be used as solvents for extraction of propolis. Extraction is typically performed at a temperature above the melting point of the extracting oil or solvent.

In some embodiments, extraction is performed at a temperature below 5, 10, 15, 20 or 25° C., using a cold-pressed oil, or in the presence of antioxidants such as vitamin E, ascorbyl palmitate, BHT, or BHA. This preserves components that might otherwise be oxidized.

In some embodiments, Brazilian green propolis is extracted or suspended in an oil or non-ionic solvent without separation of solids. This provides soluble materials in an oily phase of the solvent/propolis mixture. The extraction of these materials makes it easier to expose them to teeth surfaces, regardless of the presence of other insoluble propolis components.

In other embodiments, solids are separated from the oil fraction, for example, by filtration, sedimentation or centrifugation to provide separate oily fraction containing compounds extracted from the propolis and residual solid material that did not dissolve in the oil. This facilitates standardization of the propolis oil based on levels of its various components by removing insoluble components. It also permits a propolis oil to be fortified with these extracted components, for example, to containing 2, 3, 4, 5, 6, 7, 8, 9, 10 or more than 10-times the amounts of these components in a fortified propolis oil.

Propolis oil also may be further diluted, preferably to a standardized concentration of at least one of its ingredients, by addition of one or more oils or other excipients or carriers.

In some embodiments, the propolis oil may be formulated as an emulsion or suspension containing an aqueous phase. For example, propolis oil may be formulated as an emulsion in combination with a physiological acceptable medium or with artificial saliva.

A propolis composition may be formulated as a salve, ointment or cream containing propolis oil and other oily ingredients. An ointment or salve is a homogeneous, viscous, semi-solid preparation, most commonly predominantly a greasy, thick oil with a high viscosity. An ointment may contain various bases including absorption bases, e.g., beeswax and wool fat; emulsifying bases, e.g., cetrimide and emulsifying wax; hydrocarbon bases, e.g., ceresine, microcrystalline wax, hard paraffin, and soft paraffin; vegetable oil bases, e.g., almond oil, coconut oil, olive oil, peanut oil, and sesame oil; and/or water-soluble bases, e.g., macrogols 200, 300, 400.

Creams are semi-solid emulsions of oil and water. They are divided into two types: oil-in-water (O/W) creams which are composed of small droplets of oil dispersed in a continuous water phase, and water-in-oil (W/O) creams which are composed of small droplets of water dispersed in a continuous oily phase. Propolis oils as disclosed herein may be incorporated into to a cream for application to the teeth or other oral surfaces. Ointments and creams permit at least a longer temporary contact of propolis oils with teeth than a less viscous solution or oil.

Foams. Propolis oil may be incorporated into a foam, for example, in combination with an aqueous component and an emulsifier. A foam may be evenly applied and easily spread over the teeth. In one embodiment, a foamable oral care composition is provided as well as methods for administering or applying the composition to a human or animal subject.

Animals that may be treated by the methods and products disclosed herein include livestock, pets or zoo animals that have teeth susceptible to dimineralization including simians, horses, cattle, cats and dogs.

In one embodiment a liquid, foamable, dental propolis oil foam is provided. In certain embodiments, the composition is packaged in a foam generating container. The composition comprises an aqueous solution of a water soluble fluoride ion releasable salt; a surfactant selected from the group consisting of nonionic surfactants, zwitterionic surfactants, betaine surfactants, and mixtures thereof. Water employed in the preparation of commercially suitable dental foams and other water-containing compositions disclosed herein should preferably be deionized and free of organic impurities.

Surface active agents include components that may function as a surfactant, emulsifier, and/or foam modulator. Surface active agents generally increase prophylactic action by thoroughly dispersing the propolis oil throughout the oral cavity. Suitable emulsifying agents include those that are reasonably stable and foam throughout a wide pH range. The organic surface-active material is preferably selected from nonionic and zwitterionic surfactants. Mixtures of surfactants can also be used. In certain embodiments, oral compositions contain one or more surfactants in the range of about 0.1% to about 3%, and preferably of about 0.6% to about 1.5%, wherein all percentages are by weight based on the total weight of the oral composition. Suitable nonionic surfactants include ethylene oxide/propylene oxide block copolymers (e.g., Poloxamers or Pluronic™. surfactants); polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and condensates of sorbitan esters of fatty acids with ethylene oxide (polysorbates).

Non-limiting examples of sorbitan ester ethoxylates include sorbitan fatty acid esters with of about 20 to about 60 moles of ethylene oxide (e.g. the Tween™. surfactants, a trademark of ICI Americas, Inc., Wilmington, Del., U.S.A. Particularly preferred polysorbates are Polysorbate (polyoxyethylene 20 sorbitan monolaurate, Tween™ 20) and Polysorbate 80 (polyoxyethylene 20 sorbitan mono-oleate, Tween™80).

Suitable poloxamer surfactants include poly(oxyethylene) poly(oxypropylene) block copolymers having an average molecular weight of about 3,000 to about 15,000. Intermediate average molecular weights may be of about 6,000 to about 15,000 with a preferred average molecular weight of about 10,000 to about 15,000. Such copolymers are known commercially by the non-proprietary name of poloxamers, the name being used in conjunction with a numeric suffix to designate the individual identification of each copolymer. Poloxamers have varying contents of ethylene oxide and propylene oxide, resulting in a wide range of chemical structures and molecular weights. One preferred poloxamer is Poloxamer 407, available, for example, under the tradename Pluronic F127 by BASF of Mount Olive, N.J., U.S.A.

Zwitterionic surface active agents can be broadly described as those containing both a negative and a positive charged group. In various embodiments, they are derivatives of aliphatic quaternary ammonium, phosphonium, and sulfonium compounds, in which the aliphatic radicals can be straight chain or branched of about 8 carbons or more, and preferably 8 to about 18 or 20 carbons. The positively charged group is typically a quaternary ammonium group, while the negatively charged group is generally an anionic water-solubilizing group such as carboxy, sulfonate, sulfate, phosphate or phosphonate. One example of a suitable of a suitable zwitterionic surfactant is 4-(N,N-di(2-hydroxyethyl)-N-octadecylammonio)-butane-1-carboxylate.

Water and oil based compositions. In some embodiments, the propolis oil is formulated as a cream, paste or other lipid-containing composition such as a micelle or liposome. Dispersions of the propolis oil may be prepared in glycerol, liquid polyethylene glycols, and mixtures thereof and in more or other oils. Under ordinary conditions of storage and use, these preparations contain a preservative to prevent the growth of microorganisms. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Liposomes. Propolis oil may also be formulated as liposomes which may be formulated as microparticles or nanoparticles. Emulsifiers which can be used to emulsify propolis oil and water into an oil-in-water emulsion include polysorbates which are a class of emulsifiers often used in pharmaceutical, food, and cosmetic products. Polysorbates are oily liquids derived from ethoxylated sorbitan (a derivative of sorbitol) esterified with fatty acids. Some representative polysorbates are Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate) and Polysorbate 80 (polyoxyethylene (20) sorbitan monooleate). One preferred emulsifier for use in producing the oil-in-water emulsions disclosed herein is polyoxyethylene sorbitan monolaurate. Other food grade emulsifiers include lecithin, sodium phosphates and mono- and di-glycerides. In preferred embodiments, the emulsifier is an E20 food grade emulsifier (polyoxyethylene [20] sorbitan monolaurate; Tween 20®) which is incorporated into the essential oil-in-water emulsion in amounts of 0.1 to 8.0 vol/vol %, and preferably between 1.6-2.0 vol/vol %.

A food grade emulsifier, such as polyoxyethylene sorbitan ester like polyoxyethylene sorbitan monolaurate (Tween 20®), is able to create a homogeneous dispersion of the components present propolis oils and help standardize their functional effects, such as tooth or enamel hardening or pain reduction. Such an emulsifier is acceptable as a food additive and may be incorporated into the liposome compositions disclosed herein in amounts of 0.1, 0.2, 0.5, 1, 2, 5 to 8.0 vol./vol %, and preferably between 1.6-1.8-2.0 vol./vol %, is safe based on acceptable daily intake of up to 25 mg/day of such food grade emulsifiers in foods suggested by WHO in 1974.

An emulsion is a fluid system in which liquid droplets are dispersed in a liquid. One component of the liposome composition disclosed herein is an essential oil-in-water emulsion which is encapsulated in liposomes. Oil droplets in the dispersed phase of the essential oil-in-water emulsion disclosed herein may range from 10, 50 100, 200, 500, <1,000 nm (nanoemulsion) or 1,000 nm (1 µm), 2, 5, 10, 20, 50 to 100 µm (macroemulsion). Preferably, the average diameters of oil droplets of the essential oil-in-water emulsions are less than 1,000 nm. The droplet size in the essential oil-in-water emulsion may be increased or decreased to modify the pharmacokinetic rate of release of propolis oils and their components when administered to a subject. In some embodiments, the nanoemulsion is stable at room temperature for at least 3, 6, 9 or 12 months. In another embodiment, the nanoemulsion releases about 20, 30, 40, 50, 60 or 70 wt % of the essential oils over a period of 4, 6, 8, 10, or 12 hours when applied to the nostrils or to the nasal mucosa.

Dental varnish. Dental varnish compositions, for example, for application of fluorides to teeth, and methods for their application are known and incorporated by reference to Allred, et al., U.S. Patent Publication 2018011694 and to Blanvalet, et al., U.S. Patent Publication 20160303007. Some varnishes, including those incorporating propolis oil, may be left in place on or around the teeth for days or weeks. These varnishes can comprise a stable liquid or gel carrier and an active agent, such as Brazilian green propolis oil, dispersed within the carrier.

The carrier may comprise a solvent, a resin component and an acidifying component. Examples of the resin component include colophony, polyurethane, resin modified glass ionomer, methyl salicylate, and polyamide. In some embodiments a natural resin may be used such as natural film-forming ingredients such as shellac or shellac wax. Exemplary artificial resins include Foral® NC or CX resins, see hypertext transfer protocol secure://www.eastman.com/Brands/Foral/Pages/Overview.aspx (last accessed Mar. 30, 2020, incorporated by reference). In some embodiments, an existing dental varnish, such as one used to apply fluoride, may be modified to incorporate or substitute propolis oil for the active ingredient. Other suitable resins may be selected by those in the art and many are commercially available.

In some embodiments, the varnish may contain an organo phosphoric acid to increase adhesiveness of the varnish to teeth. Such a varnish may optionally contain a source of calcium ions, phosphorous ions, or fluoride ions. A varnish may be formulated to be anhydrous to minimize interaction of its components. A varnish may be formulated to release propolis oil or its active components over a period of time such as over a period of 1, 2, 3, 4, 5, 6, 7, 8, 9, 10, 11 or 12 weeks.

Pastes. Propolis oil may be added to existing toothpaste formulations. Toothpastes typically contain 20-42% water, abrasives, and detergents. Many contain fluoride as well for example at concentrations of 1,000 to 1,500 ppm. Various formulations of toothpastes are known and commercially available. Compositions and functions of toothpastes are also incorporated by reference to hypertext transfer protocol secure://en.wikipedia.org/wiki/Toothpaste (last accessed Mar. 31, 2021). Other types of pastes, such as those that can be directly applied to teeth may also be formulated to contain propolis oil or its fractions.

Abrasives include aluminum hydroxide, calcium carbonate, calcium hydrogen phosphates, silicas, zeolites, hydroxyapatite or white mica. Abrasives often constitute 40 to 60% of a toothpaste. Toothpastes have a relative dentin abrasivity (RDA) set by the standards DIN EN ISO 11609. An RDA of no more than 50 is often recommended for toothpastes used daily to minimize abrasion of the teeth. Sodium lauryl sulfate is a common detergent used in toothpastes, though other surfactants may be used. Toothpastes may also incorporate antimicrobial agents such as triclosan or zinc chloride. Flavorants and remineralizers such as hydroxyapatite crystals or calcium phosphates may be included. Toothpastes may also incorporate glycerol, xylitol, sorbitol, or zylitol, strontium chloride or potassium nitrate or arginine or calcium sodium phosphosilicate to alleviate dentinal hyper sensitivity. In some embodiments of the invention 0.1 to 5% of propolis oil may be incorporated into a toothpaste, toothpowder or tooth polish.

In some embodiments, the propolis oil or its fractions may be formulated with one or more of potassium nitrate and stannous fluoride in amounts of from 0.5 to 10 wt. % based on the total weight of the composition, preferably 1 to 5 wt. %; with or without an antimony compound such as antimony (V) metasilicate, antimony potassium tartrate, antimony(III) acetate, antimony(V) pentachloride, antimony(V) hydrogen carbonate, antimony(III) oxalate, antimony(III) trifluoride and/or antimony potassium oxalate in amounts that are preferably less than 10 mg of the Sb compound per kg of toothpaste, more preferably 0.5-25 mg/kg or 1-10 mg/kg. Propolis oil or its fractions may be incorporated into whitening toothpastes, which may contain hydrogen peroxide or carbamide peroxide, or mica, or fluoride-containing toothpastes.

Other active ingredients and formulations. In some embodiments, propolis oil or its fractions may be administered along with, or incorporated into a composition, containing another active ingredient. These include calcium and phosphorous salts or acids, fluorides, sugar alcohols like xylitol, erythritol, or sorbitol, which inhibit acid production by oral microorganisms and can stimulate saliva flow; hydroxyapatite (which may contain carbonate, fluoride, and magnesium) are the most common heteroionic substituents and biomimetic glass or ceramic particles which can promote remineralization, and bioactive peptides such as oligopeptide P11-4, which is a synthetic, pH controlled self-assembly peptide used for biomimetic mineralization. In other embodiments, propolis oil may be formulated as a toothpaste, tooth polish, tooth powder, mouthwash, dental floss, dental tablet, chewing gum, gingival message crème, gargle tablet, lozenge, dental paste or topical gel.

In some embodiments, it may be added to a food or beverages.

Propolis oil or its fractions may be incorporated into fatty foods such as vegetable oils (e.g., cooking oils, salad oils, animal fats, vegetable shortenings, etc.), milk products (e.g., cheese, butter, cream, milk, chocolate milk, kefir, yogurt), baked or cooked foods (breads, crackers, pizza, cakes, cookies), vegetable milks, nut or peanut butters, tahini, or hummus. It may be incorporated into sugars, syrups, molasses, or honey. It may be incorporated into chewing gum, candy or chocolates or chocolate products. It may be incorporated into breath mints or cough drops or similar products. Consumption of these foods would bring the propolis oil or its components into contact with teeth.

Propolis oil or its fractions may be incorporated into beverages including the milk products described above, soft drinks including carbonated drinks or drinks containing phosphoric acid, coffee, tea, herbal teas or infusions, energy drinks, exercise recovery drinks, fruit or vegetable juices, including apple juice, orange juice, grapefruit juice, pineapple juice, tomato juice.

Propolis oil or its fractions may be incorporated into animal feeds including dog or cat chews or kibbles that clean or harden teeth.

Propolis oil or its fractions may be incorporated into these foods, beverages or other products disclosed herein in amounts such as 0.001, 0.002, 0.005, 0.01, 0.02, 0.05, 0.1, 0.2, 0.5 or >0.5 wt/wt % or v/v %.

Demineralization of the tooth, including enamel and dentin, is a complex phenomenon which is influenced by multiple factors including a patient's health, cumulative salivary flow, and dietary habits, as well as the nature of the oral microflora. Often it is caused by exposure of a tooth or teeth to an acid environment, such as one having a pH of 5.0, 5.5, 6.0, 6.5, or below. Acid exposure may occur by ingestion of acidic foods or beverages, by gastrointestinal reflux, or by acids produced by microorganisms. Common sources of acid exposure or demineralization include bacterial plaques; frequent ingestion of acidic beverages such as phosphoric acid, which is a common ingredient in soda or diet soda, sports drinks and flavored water, can demineralize teeth; frequent exposure of the teeth to citrus fruits, which contain citric acid (particularly lemons); or frequent exposure of teeth to stomach acids (for example, from an eating disorder, bulimia and patients with reflux disorders). Certain drugs such as methamphetamines (meth), whether from the drug itself, poor nutrition, chronic dry mouth or xerostomia caused by the drug, or poor dental hygiene common in drug abusers can promote demineralization. Lack of saliva and a resulting dry mouth is a common side effect of many medical conditions and medications including various types of chemotherapy. Poor dental hygiene while undergoing orthodontic treatment frequently results in white spot lesions or enamel demineralization. Infection/inflammation is a cause of the isolated white spot demineralized areas which are commonly seen on permanent incisor teeth, after a primary (baby) incisor is injured. The primary tooth root is positioned very close to the developing crown of the permanent incisor. If the primary tooth is injured and becomes inflamed at its root tip, the inflammation can demineralize the permanent incisor crown (known in such cases as Turner's hypoplasia). The products, compositions and methods disclosed herein may be used to treat demineralization associated with any of these conditions.

Demineralization is characterized by several physical features including loss or erosion of enamel or dentine thickness, formation of carious lesions, increased area or depth or carious lesions, appearance of white spot lesions, loss of calcium, phosphorous or fluorine from carbonated hydroxyapatite enamel crystal voids and by microscopic appearance, for example, by appearance of a more porous enamel structure or deeper lesions in enamel or dentine.

Remineralization is characterized by opposite effects including restoration of enamel or dentine thickness, regression of carious lesions, decreased area and depth regression of white spot lesions, deposit of calcium, phosphorous or fluorine into enamel or dentine, and by microscopic appearance, for example, appearance of a less porous enamel structure compared to demineralized enamel.

Remineralization may decrease the area and/or depth of lesions in the tooth by at least 1, 2, 5, 10, 20, 30, 40, 50, 60, 70, 80, 90 or 100% compared to the initial deminineralized surface, increase the deposit of calcium, phosphorous or fluorine into enamel or dentine by 1, 2, 5, 10, 20, 30, 40, 50, 60, 70, 80, 90, 100, or >100%, increase enamel or dentine thickness by at least 1, 2, 5, 10, 20, 30, 40, 50, 60, 70, 80, 90, 100, or >% compared to the initial deminineralized surface, may decrease the porosity or void space of an area, section or volume of a tooth by 5, 10, 20, 30, 40, 50, 60, 70, 80, 90, 100, or >100% compared to the initial deminineralized area, section or volume of the tooth, enamel or dentine. Porosity or void fraction is a measure of the void (i.e. "empty") spaces in a material, and is a fraction of the volume of voids over the total volume, between 0 and 1, or as a percentage between 0% and 100%.

Assessment of enamel may be performed using polarized light microscopy (e.g. to measure depth of lesions from enamel surface to bottom border of structural change of enamel prisms), microradiography (e.g., to measure lesion depth from enamel surface to bottom of lesion using relative decrease of gray value $\Delta gv$ compared to gray value of sound enamel), scanning electromicroscopy (to measure lesion depth from enamel surface to bottom border or structural change of enamel prisms), or X-ray microanalysis (e.g., to investigate differences in chemical content between different locations within the same tooth); see Sable, N., et al. *Demineralization of Enamel in Primary Second Molars Related to Properties of the Enamel*, SCIENTIFIC WORLD JOURNAL, 2012, Article ID 587254; hypertext transfer protocol secure ://doi.org/10.1100/2012/587254 (incorporated by reference).

Remineralization and supplemental agents. In some embodiments, teeth are further exposed to artificial saliva. Artificial saliva is commercially available and may include carboxymethylcellulose, glycerin, minerals such as potassium or sodium salts, phosphates, calcium, fluorides, and xylitol.

Teeth may also be exposed to concentrations, preferably aqueous solutions, of minerals such as sodium, potassium, calcium, magnesium or phosphorus-containing compounds. These include sodium or potassium chloride, sodium bicarbonate, calcium salts (e.g., calcium chloride), magnesium salts, phosphorous-containing compounds (e.g., monobasic sodium phosphate, dibasic sodium phosphate), calcium-phosphates, calcium-silicates, or zinc or iron salts. They may also be exposed to fluorides as well as vitamins such as vitamin D or vitamin K. In some embodiments, these materials may be suspended in propolis oil or a non-polar medium. In other embodiments, amino acids such as lysine or arginine or peptides, such as milk peptides or biomineralizing peptides, may be incorporated. Preferably, propolis oil is administered with substrates for remineralization of enamel and dentin such as calcium salts or calcium phosphates that promote remineralization. One or more remineralization agents may be formulated in a composition containing propolis oil or its fractions.

The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, $21^{st}$ edition, 2005, incorporated herein by reference. Moreover, it will be understood that preparations should meet sterility, pyrogenicity, general safety and purity standards as required by FDA Office of Biological Standards.

Routes of administration. Preferably, the propolis compositions disclosed herein are administered to a site or surface that is at risk of, is, or has undergone demineralization. A propolis oil composition can be evenly applied over the entire surface of the tooth or teeth to be treated, by swabbing, dabbing, varnishing, painting, rinsing, soaking, spraying, or foaming. In some embodiments, the propolis oil composition that is placed in a tray that is held around the teeth for a time sufficient for remineralization or hardening of the enamel or other portions of the teeth compared to untreated teeth or enamel.

Exposed surfaces of a tooth, including surfaces with caries, carious lesions, cavities, interproximal regions, and exposed roots of teeth may be contacted with the propolis oil composition. After a treatment, a subject may be asked not to rinse, eat or drink for at least 15, 30, or 60 minutes to allow the teeth to interact or absorb the propolis oil and help harden or remineralize demineralized areas. Preferably, the exposed surface of a tooth is treated with propolis oil prior to complete erosion of the enamel. In some embodiments, enamel thickness may be measured by caliper such as a digital caliper or by using laser optics, see Fried, D. et al., *Monitoring tooth demineralization using a cross polarization optical coherence tomographic system with an integrated MEMS scanner*, Proc. SPIE Int Soc Opt Eng, 2012, 8208: 820801; hypertext transfer protocol secure://dx-.doi.org/10.1117%2F12.914599 (incorporated by reference). Such methods may be used to assess or quantify remineralization of a tooth or portion thereof compared to normal healthy teeth or compared to a subject's teeth prior to treatment.

Another method to quantify remineralization of teeth involves performing a surface roughness analysis. As a general rule, first baseline surface roughness values are noted via non-contact profilometry. Second, the enamel surface is demineralized and roughness values are noted again. Demineralization increases the roughness of enamel surface because ions leach out of enamel at low pH. In a final step, remineralizing solution/oil or paste (e.g., propolis) is applied to the enamel surface via simulated brushing and roughness values are noted again. If the remineralizing oil is efficient, a reduction in surface roughness values of enamel is noted when post-remineralization values are compared with post-demineralization values.

Enamel thickness is different for different teeth. Even in a single tooth, it is different at various surfaces. For example, in the anterior teeth, it is thicker at the incisal edges and thinner at the cervical margin (near cementum-enamel junction). For the posterior teeth, it is more on the cusps (around 2.5 mm) and again it is thinner at the cervical margin. Demineralization depends on several factors including the type of demineralization solution used, its pH, and time period for which the enamel surface is exposed to it.

In some embodiments, prior to application of a propolis oil composition, the teeth may be cleaned so as to remove plaque or tartar and proteins, carbohydrates or oils from their surfaces or may be dried so as to facilitate contact between the surface of the teeth and the propolis oil composition.

Microhardness may be determined using methods known in the art or those shown in the Example below. Functionally equivalent equipment to that used in the Example may be employed. In some embodiments of the invention microhardness (VHN or average VHN) of demineralized tooth enamel prior will range from <100, 150, 200, 250, 300, 350, 400, 500, 550, or 600 and post propolis oil treatment microhardness will be increased by at least 5, 10, 20, 30, 40, 45 or 50%. As described above, other measures of microhardness, including reductions in surface roughness via non-contact profilometry can also be used.

Dosage. Propolis oil, as produced by extraction of propolis with an oil, such as a canola oil, may be applied undiluted to teeth or incorporated undiluted into a composition. In other embodiments, the propolis oil may be diluted with oil, water or another material to a concentration of 1, 2, 5, 10, 20, 30, 40, 50, 60, 70, 80, 90, 95 or <100 wt %. In another embodiments, components of propolis oil that phase partition out of oil, such as into a aqueous buffer or alcohol-aqueous solution, such as ODEP, can be resuspended to the original volume or weight of the extracting oil or further diluted or concentrated, e.g., to 0.1, 0.2, 0.5, 1.0, 2.0, 5.0, 10.0 or >10.0-times of the original wt/wt or v/v concentration.

A dose of 0.1, 0.2, 0.5, 1.0, 2.0 or 5.0 ml of propolis oil, for example, as extracted in vegetable oil from Brazilian green propolis as disclosed herein, may be administered in undiluted form or as part of a composition.

Example

As shown below, the inventors investigated the effects of applying Brazilian green propolis oil to the surfaces of teeth and have shown that it re-mineralizes and hardens tooth enamel.

Twenty enamel blocks (N=20) were randomly divided into two groups (n=10). In group 1 (control), enamel blocks were brushed with artificial saliva (AS). In group 2, they were brushed with propolis oil. All the blocks were demineralized by exposing them to 6 wt % citric acid (pH: 2.2) for 5 min. Brushing was performed inside a tooth brushing simulation machine with manual toothbrushes. Each sample received 5,000 linear strokes. Surface microhardness analysis was performed for each sample at three time intervals (pre-demineralization or baseline, post-demineralization, and post-remineralization) to obtain the Vickers hardness numbers (VHNs).

An enhancement in the microhardness of the enamel samples was observed after brushing with propolis oil when compared with brushing using artificial saliva (AS) alone. In group 1 (control group), the mean baseline VHN was 583.66. It decreased to 116.23 after demineralization and increased to 184.02 after remineralization. The mean baseline VHN of group 2 was 506.91. It decreased to 317.60 after demineralization and increased to 435.19 after remineralization. The VEIN values of both the groups revealed statistically significant differences (p<0.05) in inter-group and intra-group comparisons. As shown below, brushing of enamel blocks with propolis led to a greater enhancement in their microhardness levels when compared with the control group.

Materials and Methods Propolis oil was used in the brushing experiments. Artificial saliva (AS) formulation AS was produced by mixing 0.400 g NaCl and KCl, 0.69 g $NaH_2PO_4 \cdot H_2O$, 0.79 g $CaCl_2 \cdot H_2O$, and 0.005 g $Na2S \cdot 9H_2O$ in 1000 mL of deionised water. The pH of the newly synthesized AS was 5.4, which was adjusted to a neutral pH of 7.0 by adding 1 M of NaOH.

Preparation and grouping of enamel blocks. Twenty extracted human third molars (N=20) were acquired from the dental hospital of the institute. Teeth that were devoid of white spot lesions, cavitation, and restorations were carefully selected.

The teeth were cut mesiodistally just above the cement to enamel junction using a high-speed hand piece (EXPERTmatic® LUX E15L, KaVo Dental GmbH & Co. KG, Germany) fitted with diamond bur having a head length of 1.2 mm, a diameter of 0.3 mm, and an overall length of 19 mm (WR-13, Prima®, Prima Dental Group, Gloucester, United Kingdom).

After the teeth were cut into two sections, the roots were discarded and the anatomic crown of each tooth was entrenched in an acrylic block ensuring that only the buccal surface of the enamel was exposed. With the help of a nail varnish, a window of approximately 4 mm×4 mm was created on this surface to ensure that all experiments and analyses were performed only in this area. As the natural contour of the enamel surface is not flat, the marked surface was ground and polished with the help of a grinding and polishing machine (MetaSery 250 Grinder-Polisher with Vector Power Head BUEHLER®, Lake Bluff, Ill., USA).

Twenty enamel blocks were randomly and equally divided into two groups.

Group 1 (control) included ten enamel blocks brushed with AS.

Group 2 included ten enamel blocks brushed with propolis oil.

Artificial demineralization. All enamel blocks were subjected to demineralization by exposing them to 6 wt % citric acid (pH: 2.2) for 5 min. To mimic dynamic in vivo conditions, glass beakers containing 500 mL of citric acid with enamel blocks completely immersed in them were placed over a rotating orbital shaker (CO-Z Orbital Shaker, USA). After the acidic challenge, enamel blocks were washed with distilled water for 1 min and were allowed to air-dry overnight.

Simulated brushing protocol. Manual toothbrushes from a single brand (Trisa®, Triengen, Switzerland) were used in this study. Tooth brushing was performed inside a brushing simulator (ZM-3.8, SD Mechatronik, Feldkirchen-Westerham, Germany). Each sample was brushed with 5,000 linear strokes, which is comparable to in vivo brushing for 6 months.[20] The load applied to the enamel samples was 250 g and the linear distance covered by the toothbrushes was set to 30 mm. After every 1,000 strokes, AS or propolis oil was added on the surface of the samples from the respective groups.

After brushing, samples were washed with distilled water for 1 min and air-dried before the microhardness measurements.

Surface microhardness analysis. Surface microhardness investigation was conducted on each sample at three time intervals: pre-demineralization (baseline values), post-demineralization, and post-remineralization.

Vickers surface hardness was calculated using a digital microhardness tester (FM-ARS 9000; Future Tech Corp, Kawasaki, Japan). Each enamel block received three indentations using a Vickers diamond indenter under a load of 250 g with a dwell time of 10 s. The average value of the three indentations was used for the analysis.

Statistical analysis. Data analysis was performed using IBM SPSS Statistics version 20.0 (IBM Corp., Armonk, N.Y., USA). Numerical data were presented as mean and standard deviation. Normality of data distribution was checked using the Kolmogorove Smirnov test. Since the data showed non-Gaussian distribution, non-parametric Wilcoxon Mann-Whitney U test was used for the comparison of microhardness between the groups. Wilcoxon signed-rank test was applied to assess the significance of the differences within each group (comparison of baseline values with post-demineralization and post-remineralization values). P-values ≤0.05 were considered statistically significant.

Figure 1:
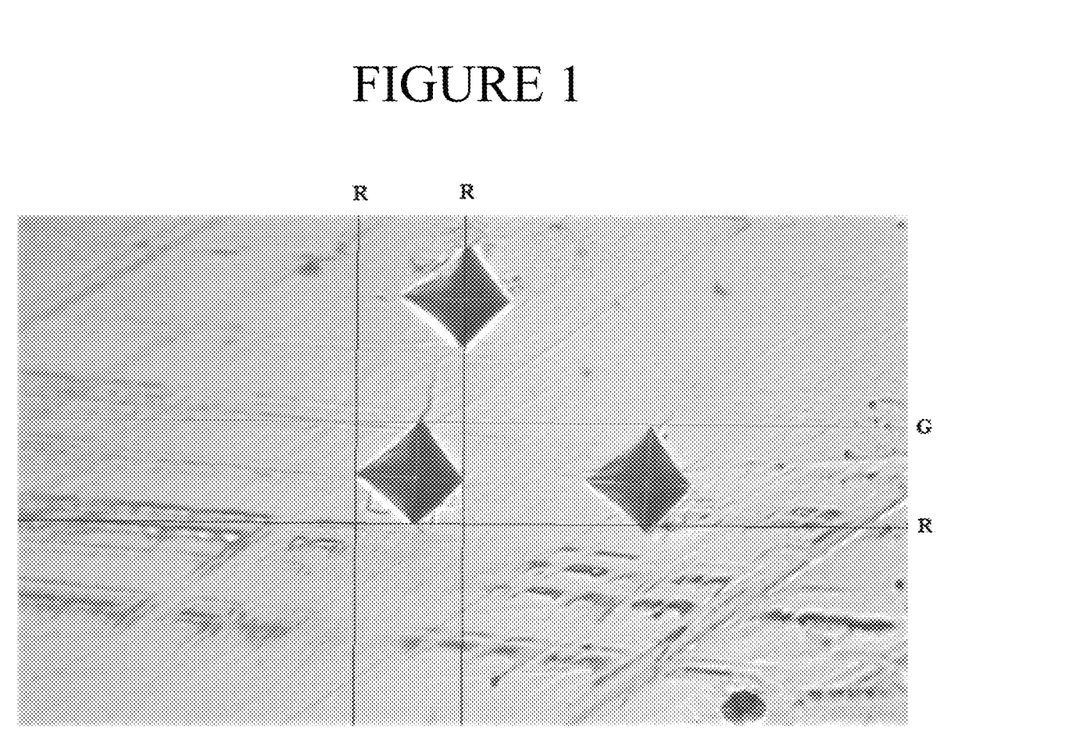
FIG. 1: Indentations on the enamel surface to obtain the Vickers hardness numbers. Propolis and remineralization of enamel.

The microhardness of the enamel blocks was assessed with the help of Vickers indentation. Each sample received three indentations (FIG. 1) on the marked unexposed buccal surface. An enhancement in the microhardness levels was observed in both Group 1 and Group 2 after brushing. Although brushing with AS in group 1 resulted in remineralization of the enamel surface after artificially induced demineralization, the improvement in the microhardness levels after remineralization was lower than that in Group 2 (Table 1).

The mean Vickers hardness number (VHN) in Group 1 (AS group) was 583.66 at baseline, 116.23 after demineralization, and 184.02 after brushing.

The mean VHN in Group 2 (propolis group) was 506.91 at baseline, 317.60 after demineralization, and 435.19 after brushing.

Significant differences were observed in the inter-group and the intra-group comparisons

TABLE 1

Mean VHN values for both groups measured at baseline, after demineralization, and after brushing

| Microhardness | Vickers hardness number mean (standard deviation) | | P-value |
| --- | --- | --- | --- |
| | Group-1 | Group-2 | |
| Baseline | 583.66 (15.80)$^a$ | 506.91 (87.41)$^a$ | 0.012 |
| Post-demineralization | 116.23 (6.84)$^{a,b}$ | 317.60 (82.06)$^{a,b}$ | 0.001 |
| Post-brushing | 184.02 (32.94)$^{a,b}$ | 435.19 (105.44)$^a$ | 0.001 |
| ˆP-value | 0.012 | 0.012 | e |
| ˆˆP-value | 0.012 | 0.208 | e |

ˆP-value: Within-group significance (baseline versus post-demineralization).
ˆˆP-value: Within-group significance (baseline versus post-brushing).
$^a$Denotes the significance of means in the horizontal direction (inter-group) by employing the Wilcoxon Mann WhitneyU test at 5% level of significance.
$^b$Denotes the significance of means in the vertical direction (intra-group) by employing the Wilcoxon signed-rank test at 5% level of significance.

As shown above, propolis oil surprisingly induced remineralization of teeth after induced demineralization of human enamel according to the surface microhardness analysis. While not being bound to any particular theory or explanation, these results are consistent with Brazilian green propolis oil enhancing the availability of calcium and phosphate minerals to remineralize teeth. Dental enamel is composed of HAP crystals which are primarily made up of calcium and phosphate minerals. The application of propolis oil may enhance the absorption of these minerals back into the enamel surface after brushing or affect the volume or composition of dental biofilm, resulting in enhanced remineralization. Regardless of the mechanism of remineralization, the results above show that propolis oil has the ability to remineralize teeth and increase the microhardness of their enamel surfaces.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

As used herein, the term "and/or" includes any and all combinations of one or more of the associated listed items and may be abbreviated as "/".

All ranges disclosed herein, unless otherwise specified, include both endpoints as well as subranges and specific values within the range. Thus, a range of 1 to 20% would include 1 and 20 as well as integer values 2, 3, 4, 5, 6, 7, 8, 9, 10, 11, 12, 13, 40, 15, 16, 17, 18 and 19 as well as fractional values within this range.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. The recitation of one or more preferred embodiments does not imply that other embodiments are not useful, and is not intended to exclude other embodiments from the scope of the technology. As referred to herein, all compositional percentages are by weight of the total composition, unless otherwise specified.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for remineralizing teeth, comprising:
    extracting a propolis of Brazilian green into an oil to form a Brazilian green propolis oil;
    wherein the Brazilian green propolis oil consists of the oil and the propolis of Brazilian green;
    contacting a tooth of a subject with only the Brazilian green propolis oil for a time and under conditions to increase Vickers Hardness of the tooth or a portion thereof by at least 5%.

2. The method of claim 1, wherein remineralizing comprises remineralizing enamel.

3. The method of claim 1, wherein remineralizing comprises remineralizing dentin or cementum.

4. The method of claim 1, wherein remineralizing comprises remineralizing dentin.

5. The method of claim 1, wherein remineralizing comprises remineralizing a cane, carious lesion, cavity, or exposed root of a tooth.

6. The method of claim 1, wherein the subject has reduced saliva flow or quantity.

7. The method of claim 1, wherein the subject's saliva two hours after eating or drinking is less than pH 7.

8. The method of claim 1, wherein the oil is a vegetable oil.

9. The method of claim 1, wherein the oil is a canola oil.

10. The method of claim 1, wherein the propolis of Brazilian green comprises 0.01 to 5 wt % of phenolic acids or other phenolic compounds.

11. The method of claim 1, wherein the propolis of Brazilian green comprises 0.01 to 5 wt % of flavonoids.

12. The method of claim 1, wherein the propolis of Brazilian green comprises 0.01 to 5 wt % of Artepillin C.

13. The method of claim 1, wherein said teeth are contacted with the Brazilian green propolis oil for at least 10 minutes.

* * * * *